United States Patent [19]

Hibino et al.

[11] Patent Number: 5,360,699
[45] Date of Patent: Nov. 1, 1994

[54] PHOTOCHROMIC MATERIAL AND AN OPTICAL STORAGE MEDIUM USING THE SAME

[75] Inventors: Junichi Hibino, Hirakata; Eiji Ando, Katano, both of Japan

[73] Assignee: Matsushita Electric Industrial Co. Ltd., Osaka, Japan

[21] Appl. No.: 52,867

[22] Filed: Apr. 23, 1993

Related U.S. Application Data

[63] Continuation of Ser. No. 770,650, Oct. 3, 1991, abandoned.

[30] Foreign Application Priority Data

Oct. 5, 1990 [JP] Japan .................. 2-269117

[51] Int. Cl.$^5$ .............................. G03C 1/73
[52] U.S. Cl. .................. 430/345; 430/19; 430/495; 430/962; 430/945; 252/586
[58] Field of Search .......... 430/345, 19, 495, 962, 430/945; 252/586; 548/409

[56] References Cited

U.S. PATENT DOCUMENTS

| | | | |
|---|---|---|---|
| 4,780,393 | 10/1988 | Frommeld | 430/292 |
| 4,794,068 | 12/1988 | Miyazaki et al. | 430/495 |
| 4,845,021 | 7/1989 | Miyazaki et al. | 430/495 |

FOREIGN PATENT DOCUMENTS

| | | | |
|---|---|---|---|
| 0414476 | 2/1991 | European Pat. Off. | |
| 62-165653 | 7/1987 | Japan | 430/270 |
| 63-207887 | 8/1988 | Japan | |
| 1-148590 | 6/1989 | Japan | 430/495 |
| 1-259353 | 10/1989 | Japan | 430/345 |

OTHER PUBLICATIONS

Hibino et al., Nippon Kagaku Kaishi, No. 10, pp. 1129-1135 (Oct. 1990).
Zakhs et al., Khim. Getesotsikl. Soedin, No. 10, pp. 1320-1326, 1977.
Hibino et al., Thin Solid Films, 210/211 (1992) pp. 562-564.
Hibino et al., Proc. 5th International Conference on LB Films GP19 (1991).

*Primary Examiner*—Charles L. Bowers, Jr.
*Assistant Examiner*—John A. McPherson
*Attorney, Agent, or Firm*—Ratner & Prestia

[57] ABSTRACT

The present invention provides a photochromic material which comprises a spiropyran compound of formula (I):

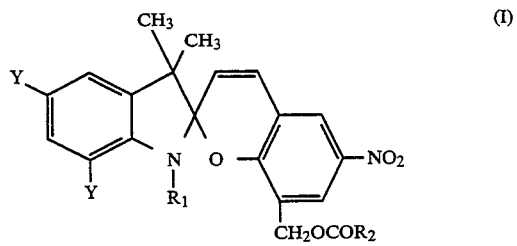

wherein $R^1$ and $R^2$ are independently alkyl groups each containing 1 to 30 carbon atoms and Y is a halogen.

The photochromic material possesses absorption sensitivity at wavelengths in the length region of about 700 nm which is the oscillation range of a semi-conductor laser device, and possesses higher stability compared with conventional one when it becomes a colored form.

7 Claims, 1 Drawing Sheet

PHOTOCHROMIC MATERIAL AND AN OPTICAL STORAGE MEDIUM USING THE SAME

This application is a continuation of application Ser. No. 07/770,650 filed Oct. 3, 1991.

BACKGROUND OF THE INVENTION

1. Field of the Invention

The present invention relates to a photochromic material and an optical storage medium using the same.

2. Description of the Prior Art

Substances which display reversible color changes upon exposure to light are collectively known as photochromic materials. Spiropyran compounds constitute one of the most intensively studied types of photochromic material.

Many spiropyran compounds have already been reported in the literature. For example, the colorless spiropyran compound (A) of the following formula is transformed into the red compound merocyanine (B) by irradiation with ultraviolet rays of wavelength approximately 340 nm. The compound (B) reverts to the form (A) if irradiated with visible light with a wavelength of approximately 580 nm.

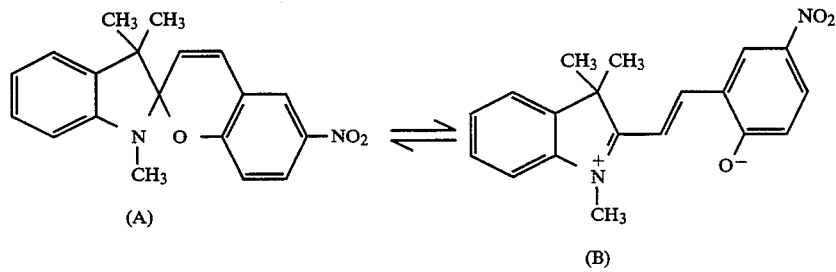

(A)       (B)

Optical storage media can be prepared by utilizing these photochromic materials which change their structures by irradiation. In order to miniaturize devices containing optical storage media, the use of semiconductor laser as a light source is generally desirable. The semiconductor lasers employed in optical storage devices ordinarily emit light in a wavelength region in the neighborhood of 700 nm, and therefore the colored form of photochromic materials used for such purposes should desirably possess absorption sensitivity in this wavelength region.

In general, either colorless forms or colored forms of photochromic materials are thermally unstable. For example, in the case of the spiropyran compound described above, colored form B is less stable than colorless form A, and the colored form reverts to the colorless form even though it is allowed to stand in the dark at room temperature. In order to overcome this problem, for example, an alkyl group is introduced into the spiropyran skeleton in Japanese Laid-Open Patent Publication No. 61-116353. When an LB film used as an optical medium is formed from the spiropyran compound into which an alkyl group is introduced, a molecular aggregate is formed. Therefore, the stability increases when the compound becomes a colored form. The colored form of the spiropyran compound, in which a molecular aggregate is formed, is highly stable compared with the conventional one, but it does not possess high sensitivity with respect to an oscillation range of a semiconductor laser (i.e., 650 nm or more). Accordingly, it is necessary to use a large amount of spiropyran compound in order to produce a device having a predetermined performance, making it difficult to miniaturize the device.

SUMMARY OF THE INVENTION

The present invention, which overcomes the above-discussed and numerous other disadvantages and deficiencies of the prior art, provides a photochromic material comprising a spiropyran compound of formula (I):

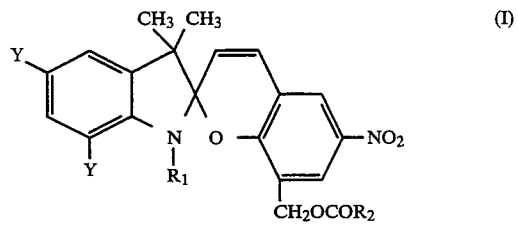

wherein $R^1$ and $R^2$ are independently alkyl groups each containing 1 to 30 carbon atoms and Y is halogen.

In a preferred embodiment, Y in formula (I) is bromine or chlorine.

In a preferred embodiment, $R^1$ in formula (I) is an alkyl group containing 6 to 30 carbon atoms, and $R^2$ in formula (I) is an alkyl group containing 9 to 23 carbon atoms.

In a preferred embodiment, $R^1$ in formula (I) is an alkyl group containing 16 to 20 carbon atoms, and $R^2$ in formula (I) is an alkyl group containing 19 to 23 carbon atoms.

The optical storage medium of the present invention comprises a substrate on which the above-mentioned photochromic material is provided in a film shape.

In a preferred embodiment, the spiropyran compound used for the optical storage medium of the present invention forms a molecular aggregate when it is made into a film.

Thus, the invention described herein makes possible the objectives of: (1) providing a photochromic material possessing absorption sensitivity in the long wavelength region, in particular, possessing absorption sensitivity at wavelengths in the length region of about 700 nm which is the oscillation range of a semiconductor laser device, and displaying reversible color changes by irradiation with light of such wavelengths; (2) providing a photochromic material possessing higher stability when it becomes a colored form compared with conventional ones; and (3) providing a photochromic material containing a spiropyran compound possessing higher stability compared with conventional ones because of the formation of molecular aggregates and possessing absorption sensitivity in an oscillation range of a semiconductor laser device.

BRIEF DESCRIPTION OF THE DRAWING

This invention may be better understood and its numerous objects and advantages will become apparent to those skilled in the art by reference to the accompanying drawing as follows.

DESCRIPTION OF THE PREFERRED EMBODIMENTS

Figure 1:
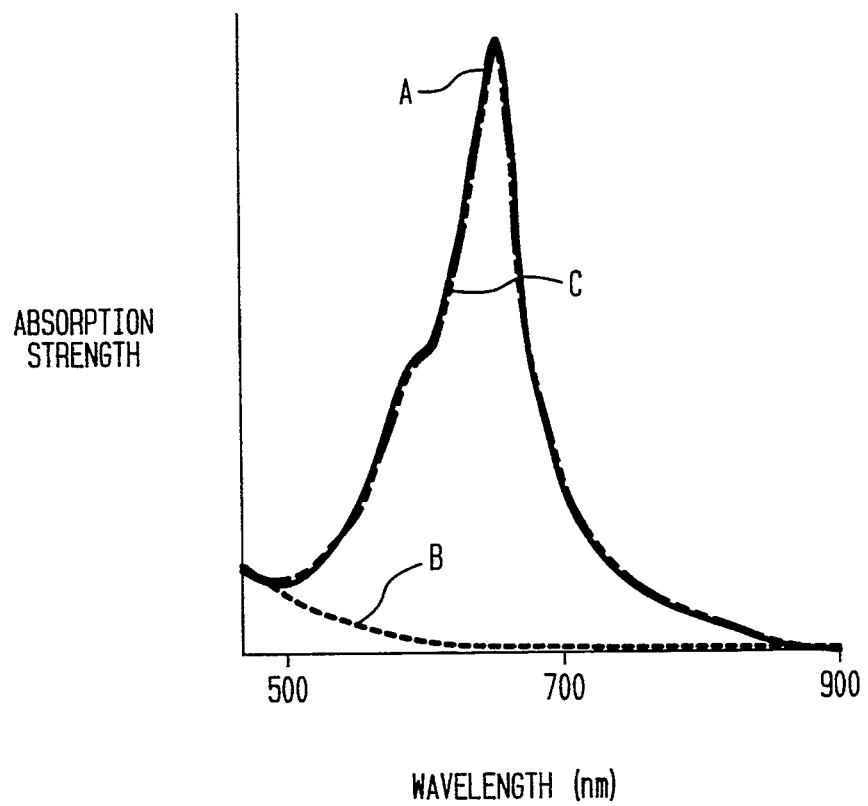
FIG. 1 is a graph showing ultraviolet visible absorption spectrums of an initial state (A) with a UV irradiation to a film of a spiropyran compound BSP1822 of the present invention, a recording state (B) recorded with a semiconductor laser device, and an erasing state (C) erased with a UV irradiation.

The inventors found that a spiropyran compound represented by the following general formula (I), having halogen groups at the 5' and 7' positions, a nitro group at the 6 position, an alkyl group at the 1' position, and an alkanoyloxymethyl group at the 8 position possesses an absorption wavelength in an oscillation range of a semiconductor laser device and the colored form thereof is thermally stable, thereby achieving the present invention.

The photochromic material of the present invention contains a spiropyran compound represented by the following general formula:

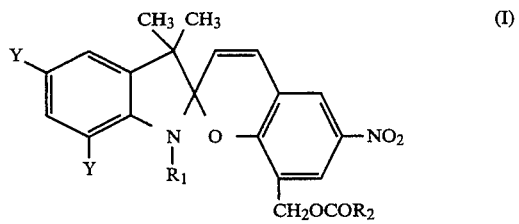

wherein $R^1$ and $R^2$ are independently alkyl groups containing 1 to 30 carbon atoms, and Y is a halogen. Preferably, $R^1$ is an alkyl group having 6 to 30 carbon atoms, and more preferably, 16 to 20 carbons atoms; $R^2$ is an alkyl group having 9 to 23 carbon atoms, and more preferably, 19 to 23 carbon atoms; and Y is bromine or chlorine.

As described in examples described later, the spiropyran compound contained in the photochromic material of the present invention can be prepared by synthesizing a spiropyran skeleton using an indolenine derivative and a salicylaldehyde derivative as starting materials, followed by halogenation. This spiropyran compound is provided onto a surface of an appropriate substrate so as to form a film. The substrate on which the film of this spiropyran compound is formed is used as an optical storage medium. The absorption wavelength of the spiropyran compound is in the range of 550 to 600 nm and has sufficient sensitivity toward a semiconductor laser beam. When the spiropyran compound is made into a film, an association of molecules occurs. Because of this, the colored form of the compound becomes thermally stable. The degree of the aggregation is related to a length of alkyl groups of $R^1$ and $R^2$. Considering readiness of the formation of the molecular aggregate, the number of the carbon atoms of $R^1$ is preferably 6 to 30, and more preferably 16 to 20, and the number of the carbon atoms of $R^2$ is 9 to 23, and more preferably 19 to 23. In particular, the spiropyran compound having $R^1$ that contains 16 to 20 carbon atoms and $R^2$ that contains 19 to 23 carbon atoms forms a stable molecular aggregate, so that the colored form thereof is highly stable when the compound is made into a film.

EXAMPLES

EXAMPLE 1

As the spiropyran compound of the present invention, a compound shown by the chemical formula (IIa), is exemplified (hereinafter referred to as BSP1822).

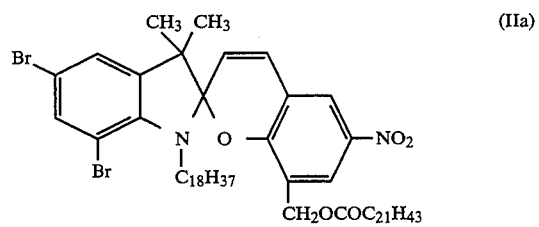

A method for the preparation of the spiropyran compound BSP1822 will be described below.

Step 1

First, 42.3 g (266 mmol) of 2,3,3-trimethyl indolenine 1 and 101.1 g (266 mmol) of iodoctadecane 2 were dissolved in 200 ml of 2-butanone, then the mixture was heated and refluxed for 40 hours. After distilling off the 2-butanone, the solid residue was recrystallized from 1000 ml of ethanol, thereby obtaining 91.5 g (197 mmol, yield 63.9%) of 1-octadecyl-2,3,3-trimethylindolenium iodide 3 in the form of a reddish-white solid. This reaction can be expressed by the following chemical equation:

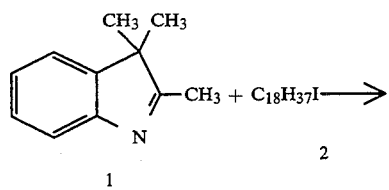

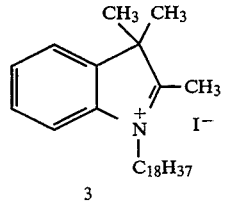

Step 2

First, 91.5 g (197 mmol) of 1-octadecyl-2,3,3-trimethylindolenium iodide 3 obtained in Step 1 was dispersed in 100 ml of diethylether, and the mixture in turn was dispersed in 400 ml of a 3.8N aqueous solution of sodium hydroxide. This suspension was then agitated for 3.5 hours, after which the oily layer was extracted with diethyl ether. After being dried over sodium hydroxide for 24 hours, the diethyl ether was distilled off, thereby obtaining 65.6 g (159 mmol, yield 80.7%) of 1-octadecyl-2-methylene-3,3-dimethylindoline 4 in the form of a yellow liquid. This reaction can be expressed by the following chemical equation:

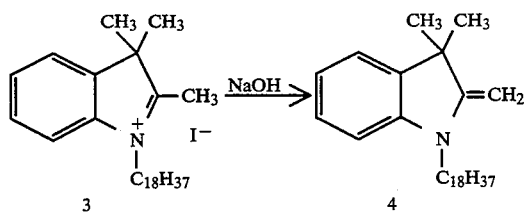

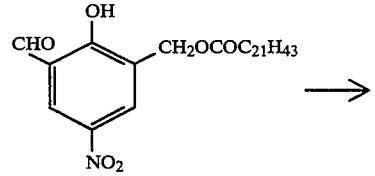

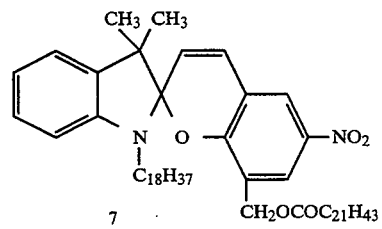

Step 3

First, 11.3 g (52.6 mmol) of 3-chloromethyl-5-nitrosalicylaldehyde) 5 was mixed with 20.6 g (52.6 mmol) of silver behenate in benzene, and this heterogeneous system was heated and refluxed for 40 hours. The reaction mixture was then filtered and the filtrate was concentrated, after which recrystallization was effected in a mixed benzene-hexane (1:5) solvent, thereby obtaining 11.1 g (21.3 mmol, yield 40.5%) of 3-docosanoyloxymethyl-5-nitrosalicylaldehyde 6 in the form of yellow needle crystal. This reaction can be expressed by the following chemical equation:

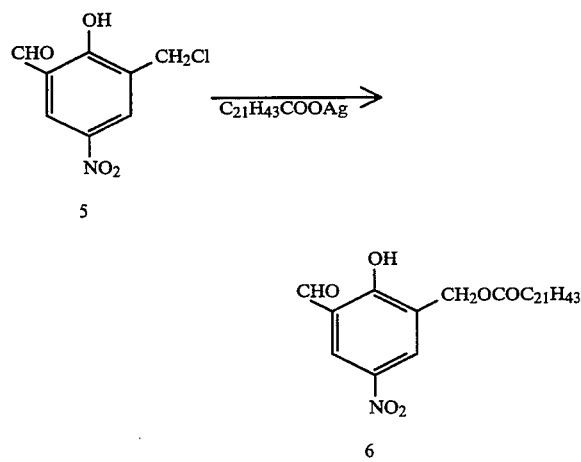

Step 4

First, 2 g (4.9 mmol) of 1-octadecyl-2-methylene-3,3-dimethylindoline 4 obtained in Steps 1 and 2 and 2.1 g (4.1 mmol) of 3-docosanoyloxymethyl-5-nitrosalicylaldehyde 6 obtained in Step 3 were heated and refluxed in 20 ml of ethanol for 1 hour. The deep green reaction mixture was then cooled and the precipitate obtained from the mixture was recrystallized three times from 80 ml of ethanol, thereby obtaining 2.5 g (2.7 mmol, yield 65.9%) of a spiropyran compound 7 as yellowish-brown crystals. This reaction can be expressed by the following chemical equation:

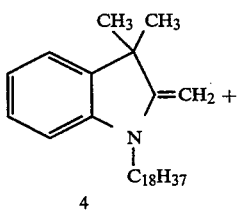

Step 5

First, 1.4 g (8.1 mmol) of N-bromosuccinimide was dissolved in a mixed solution of 75 ml of acetic acid and 75 ml of chloroform. A chloroform solution of 2.5 g (2.7 mmol) of the spiropyran compound 7 obtained in Step 4 was added dropwise to the above mixture over a period of 30 minutes. Fifteen minutes later, this reaction mixture was poured into a mixture of hexane and water and was extracted with hexane three times.

The organic layer so obtained was washed with sodium hydrogencarbonate. The organic layer was dried, concentrated and then purified by the use of column chromatography (hexane/ethyl acetate=5/1). The purified product was then recrystallized twice from hexane, thereby obtaining 2.7 g (2.5 mmol, yield 93%) of the spiropyran compound BSP1822. This reaction can be expressed by the following chemical equation:

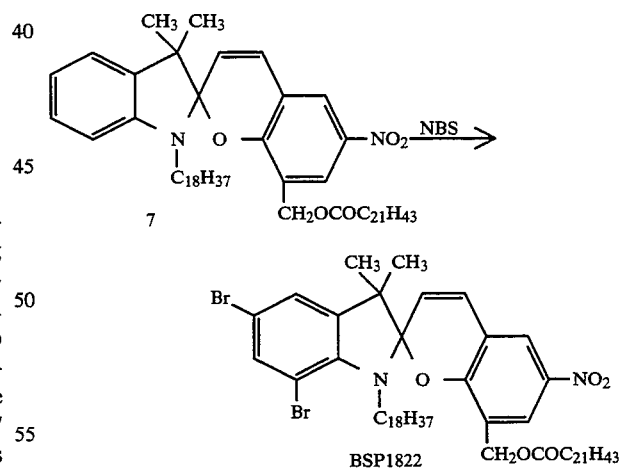

The $^1$H-NMR spectrum was measured in order to verify the structure of the final product. The result of the measurement is shown in Table 1.

TABLE 1

| $^1$H-NMR spectrum data of BSP1822 | | | |
|---|---|---|---|
| Chemical shift (ppm) | Multiplicity | Assignment | Number of protons |
| 0.88 | t | terminal methyl of long-chain alkyl J = 6.8 Hz | 6 |

TABLE 1-continued

| $^1$H-NMR spectrum data of BSP1822 | | | |
|---|---|---|---|
| Chemical shift (ppm) | Multiplicity | Assignment | Number of protons |
| 1.12 | s | 3'-methyl | 3 |
| 1.23 | s | 3'-methyl | 3 |
| 1.25 | m | methylenes in long-chain alkyls | 70 |
| 2.29 | t | methylene binding to ester carbon J = 7.6 Hz | 2 |
| 3.49 | m | methylene binding to the hydrogen of indoline skeleton | 2 |
| 4.95 | s | oxymethylene | 2 |
| 5.81 | d | 3-olefin J = 10.4 Hz | 1 |
| 6.94 | d | 4-olefin J = 10.4 Hz | 1 |
| 7.03 | d | 4'-hydrogen J = 1.6 Hz | 1 |
| 7.41 | d | 6'-hydrogen J = 1.6 Hz | 1 |
| 7.99 | d | 5-hydrogen J = 2.4 Hz | 1 |
| 8.10 | d | 7-hydrogen J = 2.4 Hz | 1 |

In Table 1, the values of chemical shift are shown in terms of ppm, and multiplicity indicated represents the form of each peak, with "s" denoting singlet, "d" doublet, "t" triplet, and "m" multiplet. The parameter J in the Assignment column represents a coupling constant.

Spiropyran compounds IIb to IIh shown in Table 2 were prepared by using the procedure in Example 1.

TABLE 2

| Spiropyran compound | $R^1$ | $R^2$ |
|---|---|---|
| IIb | $CH_3$ | $CH_3$ |
| IIc | $CH_3$ | $C_{21}H_{43}$ |
| IId | $C_6H_{13}$ | $C_{21}H_{43}$ |
| IIe | $C_{18}H_{37}$ | $CH_3$ |
| IIf | $C_{18}H_{37}$ | $C_{11}H_{23}$ |
| IIg | $C_{18}H_{37}$ | $C_{21}H_{43}$ |
| IIh | $C_{30}H_{61}$ | $C_{21}H_{43}$ |

Example 2

The spiropyran compound BSP1822 obtained in Example 1 was dissolved in benzene in a concentration of $10^{-3}$M and was spin-coated onto a quartz substrate at 2,000 rpm. Then, benzene was evaporated to form a thin film, thereby obtaining an optical storage medium. The thin film was initially colorless and was rapidly colored by irradiation with ultraviolet rays of 366 nm. The colored form of this spiropyran compound possesses an absorption maximum wavelength of 650 nm (curve A in FIG. 1), and exhibits the absorption maximum in the longer wavelength range compared with the optical storage medium using the conventional spiropyran compound. Moreover, the colored form of this spiropyran compound was highly stable and its absorbance did not change even though this compound was allowed to stand in the dark at room temperature for 24 hours. This optical storage medium could be recorded by using a semiconductor laser device having a wavelength of 670 nm (curve B, FIG. 1). This colored form of this spiropyran compound could return to the initial state (i.e., colorless state) again with irradiation of ultraviolet rays to this recorded portion (curve C in FIG. 1).

An optical storage medium was produced in the same was as in Example 1 by using any one of the spiropyran compounds IIb to IIh obtained in Example 1 in the same way as in Example 1. This optical storage medium was stable at room temperature and was capable of recording and erasing as was the medium employing BSP1822 as a spiropyran compound.

The absorption maximum wavelengths of each colored compound are shown in Table 3.

TABLE 3

| Absorption maximum wavelength of each spiropyran compound | |
|---|---|
| Spiropyran compound | Absorption maximum (nm) |
| IIb | 645 |
| IIc | 650 |
| IId | 652 |
| IIe | 650 |
| IIf | 645 |
| IIg | 650 |
| IIh | 648 |

Example 3

As the spiropyran compound of the present invention, a compound shown by the chemical formula (IIIa) is exemplified (hereinafter, referred to as CSP1822).

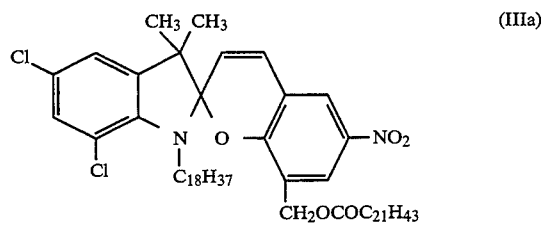

(IIIa)

A method for the preparation of the spiropyran compound CSP1822 will be described below.

First, 1.0 g (8.1 mmol) of N-chlorosuccinimide was dissolved in a mixed solution of 75 ml of acetic acid and 75 ml of chloroform. The chloroform solution of 2.5 g (2.7 mmol) of the spiropyran compound 7 obtained in Step 4 in Example 1 was added dropwise to the above mixture over a period of 20 minutes. Fifteen minutes later, this reaction mixture was poured into a mixture of hexane and water and was extracted with hexane three times. The organic layer was washed with aqueous sodium hydrogencarbonate. The organic layer was dried, concentrated and then purified by the use of column chromatography (hexane/ethyl acetate=5/1). The purified product was then recrystallized twice from hexane, thereby obtaining 2.0 g (2.0 mmol, yield 74%) of the spiropyran compound CSP1822. This reaction can be expressed by the following chemical equation:

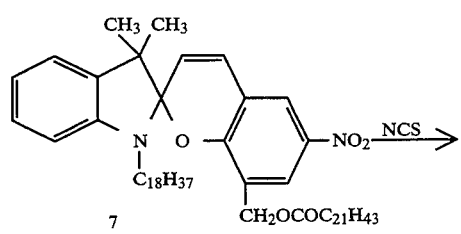

7

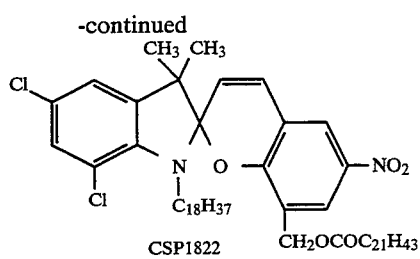

CSP1822

The $^1$H-NMR spectrum was measured in order to verify the structure of the final product.

The spiropyran compounds IIIb to IIIe shown in Table 4 were prepared by using the procedure in Example 3.

TABLE 4

| Spiropyran compound | $R^1$ | $R^2$ |
|---|---|---|
| IIIb | $CH_3$ | $CH_3$ |
| IIIc | $CH_3$ | $C_{21}H_{43}$ |
| IIId | $C_{18}H_{37}$ | $C_{21}H_{43}$ |
| IIIe | $C_{30}H_{61}$ | $C_{21}H_{43}$ |

Example 4

The spiropyran compound CSP1822 obtained in Example 3 was dissolved in benzene in a concentration of $10^{-3}$M and was spin-coated onto a quartz substrate at 2,000 rpm. Then, benzene was evaporated to form a thin film, thereby obtaining an optical storage medium. The thin film was initially colorless and was rapidly colored by irradiation with ultraviolet rays of 366 nm. The colored form of this spiropyran compound possesses an absorption maximum wavelength of 645 nm, and recording with a semiconductor laser device and erasing with ultraviolet rays were possible in the same way as in the spiropyran compound containing bromine in Example 1, and exhibited the same characteristics. The colored spirospyran compound was stable at room temperature.

An optical storage medium was produced in the same way as in Example 3 by using any one of the spiropyran compounds IIIb to IIIc obtained in Example 3. This optical storage medium was stable at room temperature and capable of recording and erasing as was the medium employing CSP1822 as a spiropyran compound.

The absorption maximum wavelengths of each colored compound are shown in Table 5.

TABLE 5

| Absorption maximum wavelength of each spiropyran compound | |
|---|---|
| Spiropyran compound | Absorption maximum (nm) |
| IIIb | 642 |
| IIIc | 640 |
| IIId | 645 |
| IIIe | 644 |

In the general formula (I), the spiropyran compound in which Y is bromine or chlorine is the most preferred. Spiropyran compounds having other halogen such as fluorine and iodine can be prepared in a similar way, and an optical storage medium exhibiting the same characteristics can be obtained.

It is understood that various other modification will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which this invention pertains.

What is claimed is:

1. A photochromic material capable of forming an aggregate having an absorption maximum near 650 nm, comprising a spiropyran compound formula (I):

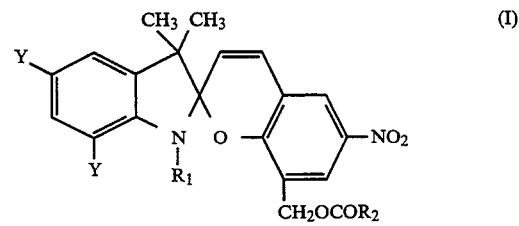

wherein $R_1$ and $R_2$ are independently alkyl groups each containing 1 to 30 carbon atoms and Y is halogen.

2. A photochromic material according to claim 1, wherein Y is bromine.

3. A photochromic material according to claim 1, wherein Y is chlorine.

4. A photochromic material according to claim 1, wherein $R^1$ is an alkyl group containing 6 to 30 carbon atoms, and $R^2$ is an alkyl group containing 9 to 23 carbon atoms.

5. A photochromic material according to claim 1, wherein $R^1$ is an alkyl group containing 16 to 20 carbon atoms, and $R^2$ is an alkyl group containing 19 to 23 carbon atoms.

6. An optical storage medium comprising a substrate on which a photochromic material according to claim 1 is provided in a film shape.

7. A photochromic material capable of forming an aggregate having an absorption maximum of at least 640 nm, comprising a spiropyran compound formula (I):

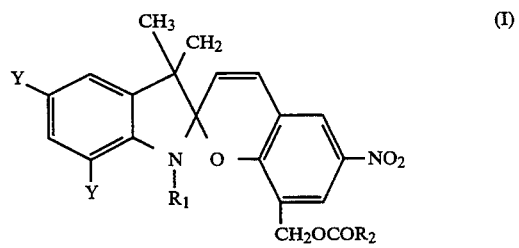

wherein $R_1$ and $R_2$ are independently alkyl groups each containing 1 to 30 carbon atoms and Y is halogen.

* * * * *

UNITED STATES PATENT AND TRADEMARK OFFICE
CERTIFICATE OF CORRECTION

PATENT NO.   : 5,360,699
DATED        : November 1, 1994
INVENTOR(S)  : Junichi Hibino et al.

It is certified that error appears in the above-identified patent and that said Letters Patent is hereby corrected as shown below:

In column 4, line 26, after "of" delete "iodoctadecane" and insert --iodooctadecane--.

In column 10, line 51, the portion of the formula reading

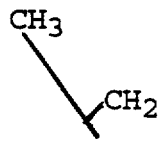

should read

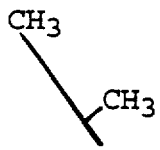

Signed and Sealed this

Ninth Day of May, 1995

*Attest:*

BRUCE LEHMAN

*Attesting Officer*     *Commissioner of Patents and Trademarks*